(12) United States Patent
Kirschman (10) Patent No.: US 8,226,720 B2
(45) Date of Patent: Jul. 24, 2012

(54) DISK AUGMENTATION SYSTEM

(75) Inventor: David Louis Kirschman, Dayton, OH (US)

(73) Assignee: X-spine Systems, Inc., Miamisburg, OH (US)

( * ) Notice: Subject to any disclaimer, the term of this patent is extended or adjusted under 35 U.S.C. 154(b) by 1025 days.

(21) Appl. No.: 11/869,009

(22) Filed: Oct. 9, 2007

(65) Prior Publication Data

US 2008/0027549 A1 Jan. 31, 2008

Related U.S. Application Data

(62) Division of application No. 10/821,823, filed on Apr. 9, 2004, now Pat. No. 7,282,065.

(51) Int. Cl.
*A61F 2/44* (2006.01)

(52) U.S. Cl. .................................................. 623/17.15

(58) Field of Classification Search .... 623/17.11–17.13, 623/17.15, 17.16, 18.11; 606/246–249, 257, 606/279

See application file for complete search history.

(56) References Cited

U.S. PATENT DOCUMENTS

| | | | |
|---|---|---|---|
| 3,786,806 A | 1/1974 | Alicandri et al. | |
| 4,309,777 A | 1/1982 | Patil | |
| 4,364,382 A | 12/1982 | Mennen | |
| 4,512,038 A | 4/1985 | Alexander et al. | |
| 4,573,458 A | 3/1986 | Lower | |
| 4,697,582 A | 10/1987 | William | |
| 4,743,260 A | 5/1988 | Burton | |
| 4,759,769 A | 7/1988 | Hedman et al. | |
| 4,834,757 A | 5/1989 | Brantigan | |
| 4,878,915 A | 11/1989 | Brantigan | |
| 4,932,975 A | 6/1990 | Main et al. | |
| 5,041,113 A | 8/1991 | Biedermann et al. | |
| 5,092,866 A | 3/1992 | Breard et al. | |
| 5,180,381 A | 1/1993 | Aust et al. | |
| 5,180,393 A | 1/1993 | Commarmond | |
| 5,258,031 A | 11/1993 | Salib et al. | |
| 5,314,477 A | 5/1994 | Marnay | |
| 5,360,430 A | 11/1994 | Lin | |
| 5,372,598 A | 12/1994 | Luhr et al. | |
| 5,375,823 A | 12/1994 | Navas | |
| 5,401,269 A | 3/1995 | Buttner-Janz et al. | |
| 5,415,661 A | 5/1995 | Holmes | |
| 5,423,816 A | 6/1995 | Lin | |
| 5,425,773 A | 6/1995 | Boyd et al. | |
| 5,480,401 A | 1/1996 | Navas | |
| 5,507,816 A | 4/1996 | Bullivant | |
| 5,540,688 A * | 7/1996 | Navas | ............................ 606/266 |
| 5,562,737 A | 10/1996 | Graf | |
| 5,562,738 A | 10/1996 | Boyd et al. | |
| 5,597,378 A | 1/1997 | Jervis | |

(Continued)

FOREIGN PATENT DOCUMENTS

FR 2681525 A1 3/1993

(Continued)

*Primary Examiner* — Eduardo C Robert
*Assistant Examiner* — David Comstock
(74) *Attorney, Agent, or Firm* — Jacox, Meckstroth & Jenkins (57) ABSTRACT

This invention relates to a disk augmentation system or situating a retainer comprising artificial supports posterior to or exterior of a spinal column and a spinal column axis. The system provides an external retainer having supports for receiving at least one artificial compression body and securing at least one artificial compression body in a supported relationship to facilitate reducing load on the one or more natural disks of a patient.

36 Claims, 4 Drawing Sheets

U.S. PATENT DOCUMENTS

| | | | |
|---|---|---|---|
| 5,601,572 A | 2/1997 | Middleman et al. |
| 5,616,144 A | 4/1997 | Yapp et al. |
| 5,645,596 A | 7/1997 | Kim et al. |
| 5,645,599 A | 7/1997 | Samani |
| 5,674,296 A | 10/1997 | Bryan et al. |
| 5,676,701 A | 10/1997 | Yuan et al. |
| 5,683,465 A | 11/1997 | Shinn et al. |
| 5,713,900 A | 2/1998 | Benzel et al. |
| 5,776,162 A | 7/1998 | Kleshinski |
| 5,779,707 A | 7/1998 | Bertholet et al. |
| 5,893,889 A | 4/1999 | Harrington |
| RE36,221 E | 6/1999 | Breard et al. |
| 5,928,284 A | 7/1999 | Mehdizadeh |
| 5,951,558 A | 9/1999 | Fiz |
| 6,022,350 A | 2/2000 | Ganem |
| 6,063,121 A | 5/2000 | Xavier et al. |
| 6,146,421 A | 11/2000 | Gordon et al. |
| 6,152,927 A | 11/2000 | Farris et al. |
| 6,231,609 B1 | 5/2001 | Mehdizadeh |
| 6,241,730 B1 | 6/2001 | Alby |
| 6,293,949 B1 | 9/2001 | Justis et al. |
| 6,419,704 B1 | 7/2002 | Ferree |
| 6,440,169 B1 | 8/2002 | Elberg et al. |
| 6,540,785 B1 | 4/2003 | Gill et al. |
| 6,572,653 B1 | 6/2003 | Simonson |
| 6,582,466 B1 | 6/2003 | Gauchet |
| 6,595,993 B2 | 7/2003 | Donno et al. |
| 6,610,093 B1 | 8/2003 | Pisharodi |
| 6,626,909 B2 | 9/2003 | Chin |
| 6,626,944 B1 | 9/2003 | Taylor |
| 6,660,007 B2 | 12/2003 | Khanna |
| 6,663,632 B1 | 12/2003 | Frigg |
| 6,669,729 B2 | 12/2003 | Chin |
| 6,835,205 B2 | 12/2004 | Atkinson et al. |
| 6,835,207 B2 | 12/2004 | Zacouto et al. |
| 6,896,676 B2 | 5/2005 | Zubok et al. |
| 7,011,685 B2 | 3/2006 | Arnin et al. |
| 7,066,957 B2 | 6/2006 | Graf |
| 2003/0009226 A1 | 1/2003 | Graf |
| 2003/0055427 A1* | 3/2003 | Graf ............................ 606/61 |
| 2003/0163132 A1 | 8/2003 | Chin |
| 2003/0171750 A1 | 9/2003 | Chin |
| 2003/0191470 A1 | 10/2003 | Ritland |
| 2005/0182400 A1 | 8/2005 | White |

FOREIGN PATENT DOCUMENTS

| | | |
|---|---|---|
| WO | 99/59492 A1 | 11/1999 |
| WO | 00/35382 A1 | 6/2000 |
| WO | 2005110257 A1 | 11/2005 |

* cited by examiner

FIG-9

DISK AUGMENTATION SYSTEM

CROSS-REFERENCE TO RELATED APPLICATIONS

This application is a division of U.S. patent application Ser. No. 10/821,823 filed Apr. 9, 2004, which is incorporated herein by reference and made a part thereof.

BACKGROUND OF THE INVENTION

This invention relates to a disk augmentation system and method for providing support for reducing load on one or more disks in a patient's spine.

Human spines are formed from vertebrae, which are separated and cushioned from each other by disks. The disks consist of a fibrous outer envelope containing a gel-like fluid. The disks are subject to large forces, which may vary from about 175 pounds when a person is at rest to as high as about 500 pounds during activity. For example, a person who lifts a 15-pound weight one foot in front of such person, using a bending movement, can generate nearly 500 pounds of force on his or her spine. Because of the high forces on them, spinal disks commonly rupture, particularly as they deteriorate with age.

Various attempts have been made to deal with the problem of a diseased intervertebral disk. One standard procedure is to remove the disk and fuse the vertebrae, which were formerly separated by the disk. A difficulty with this is that relative motion between the two vertebrae is no longer possible, causing both stiffness in the spine and difficulties in areas above or below the fused disk.

Other attempts to deal with the problem have involved removing the diseased disk and replacing it with a prosthetic artificial disk made of a resilient material or mechanical articulation. The goal of such predicate devices is to replace the diseased disk with an artificial device of similar biomechanical function. A major problem with this approach is that it requires an extensive and technically demanding surgical procedure. Such a procedure consists of surgical exposure through the abdomen of the patient, which risks injury to abdominal structures and usually requires the services of a multidisciplinary surgical team. Meticulous and complete removal of the native disk is required prior to placement of such a device—a time consuming and technically difficult procedure.

Still other attempts to deal with the problem have included devices which place springs, flexible rods, or bands around the rear portion of the spine in order to share the load placed upon disks and their associated joints. These devices have the advantage of being relatively straightforward to place surgically through a rearward approach; however, they do not replicate the ideal biomechanical properties of a true prosthetic disk system. Some examples of prior systems related to disk augmentation are illustrated in U.S. Pat. Nos. 4,309,777, 4,759,769, 5,258,031, 5,415,661, 5,645,599, 5,928,284, 6,146,421, 6,231,609, 6,293,949, 6,419,704, 6,440,169, 6,540,785, 6,595,993, 6,572,653, and 6,610,093.

There is, therefore, a need for a system and method for facilitating reducing load on one or more disks in the spinal column by providing a rearwardly-placed external disk retainer and support system and method. Such a system will replicate the biomechanical properties of an intervertebral prosthetic disk with the simplicity and safety of a rearward approach.

SUMMARY OF THE INVENTION

It is, therefore, an object of the invention to provide a disk augmentation system for providing exterior support to one or more vertebrae and to facilitate reducing load on one or more disks.

In one aspect, this invention comprises a disk augmentation system comprising: a first support for mounting onto a first vertebra in a spinal column, a second support for mounting onto a second vertebra, the first and second supports being located exterior to a disk area between the first and second vertebrae and cooperating to define a compression body area for receiving a compression body, the first and second supports supporting the compression body exterior to the disk area and permitting the first and second supports to become non-parallel during compression of the compression body, or wherein the disk augmentation system further comprises an adjustable tensioner that is adjustable after the first support is mounted to the first vertebra and the second support is mounted to the second vertebra, and wherein the compression body is generally planar.

In another aspect, this invention comprises an adjustable compression system for mounting to a plurality of vertebrae, a support for mounting on the vertebrae of a spinal column, and a retainer situated exterior of the spinal column for retaining a compression body outside a native disk space and an axis of the spine, the retainer facilitating reducing loading of at least one disk in the spinal column, the retainer comprising a first support for mounting to a first one of the vertebrae and a second support for mounting to a second one of the vertebrae, the first and second supports being adapted to permit the compression body to replicate or augment a function of a native or natural intervertebral disk by permitting the first support and the second support to become non-parallel relative to each other during use, and an adjustable tensioner for adjusting an amount of compression on the compression body between the first support and the second support after the first and second supports are mounted onto the first one of the vertebrae and the second one of the vertebrae, respectively, wherein the compression body is generally planar.

In still another aspect, this invention comprises a method for reducing load on a disk, mounting a first support on a first vertebra, mounting a second support on a second vertebra that is adjacent the first vertebra, the first and second supports defining an area for housing a compression body exterior to a disk area, and situating the compression body in the area, using an adjustor to adjust an amount of loading on the compression body after the first and second supports are mounted on the first and second vertebrae, respectively, the adjustor adjustably coupling the first support to the second support, and the first and second supports being adapted to become non-parallel during compression of the compression body.

In yet another aspect, this invention comprises an adjustable compression system for reducing a load on at least one lumbar disk in a spinal column, the adjustable compression system comprising: a retainer for mounting on a first vertebra and a second vertebra of a spinal column, the retainer comprising a first artificial body support and a second artificial body support cooperating to define a retaining area for receiving an artificial body and for supporting the artificial body posterior of the first vertebra and the second vertebra, an adjuster adjusting an amount of loading on the artificial body after the first and second supports are mounted on the first and second ones, respectively, of the vertebrae; and the retainer cooperating with the artificial body to facilitate reducing load on the at least one lumbar disk when the first and second vertebrae move either toward or away from each other, and permitting the first artificial body support and the second artificial body support to become non-parallel relative to each other to replicate or augment a function of a native disk, the artificial body being generally planar.

In still another aspect, this invention comprises an extra-axial spinal artificial disk method comprising the step of placing an artificial elastic or articulating mechanism that replicates or augments the function of a native disk in any location other than a native disk space or a normal axis of the spine.

In yet another aspect, this invention comprises an artificial disk that replicates or augments the function of a native disk in any location other than a native disk space or a normal axis of the spine, comprising: a body, and an elastomeric or articulating mechanism in the body.

In still another aspect, this invention comprises an adjustable compression system for reducing the load on at least one lumbar disk, the adjustable compression system comprising: a retainer for retaining a first compression body posterior of the spinal column and for facilitating reducing load on at least one lumbar disk in the spinal column, and a second retainer for mounting on the spinal column also for facilitating reducing load on the at least one lumbar disk, wherein the first and second retainers are not located along an axis of the spinal column.

Other objects and advantages of the invention will be apparent from the following description, the accompanying drawings and the appended claims.

DETAILED DESCRIPTION OF PREFERRED EMBODIMENT

Referring now to FIGS. 1-11, a disk augmentation system and method will now be described. The system and method of the invention are used to facilitate reducing load on one or more disks, such as disk 12 between vertebrae 14 and 16 and disk 18 between vertebrae 16 and 20. The invention comprises means or a system 22 for reducing a load on at least one of lumbar disks when the vertebrae, such as vertebrae 14 and 16, move either away from or toward each other.

Figure 3:
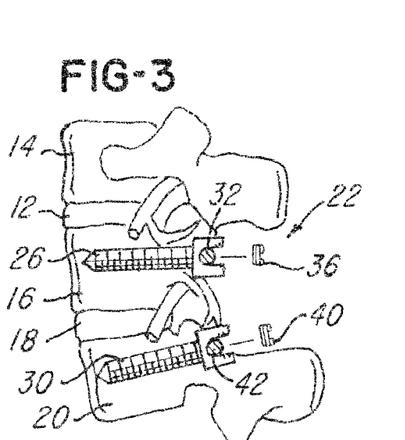
FIG. 3 is a view illustrating means and method for mounting support rods onto anchor screws.
Figure 4:
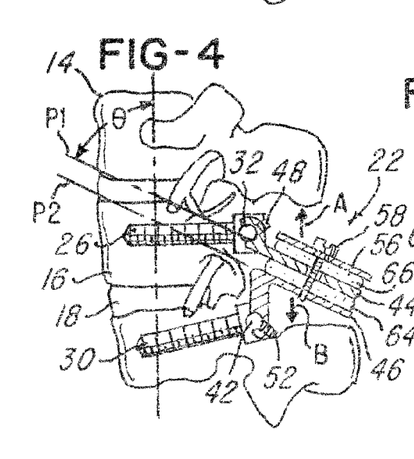
FIG. 4 is a view illustrating a retainer mounted onto the support rods.
Figure 9:
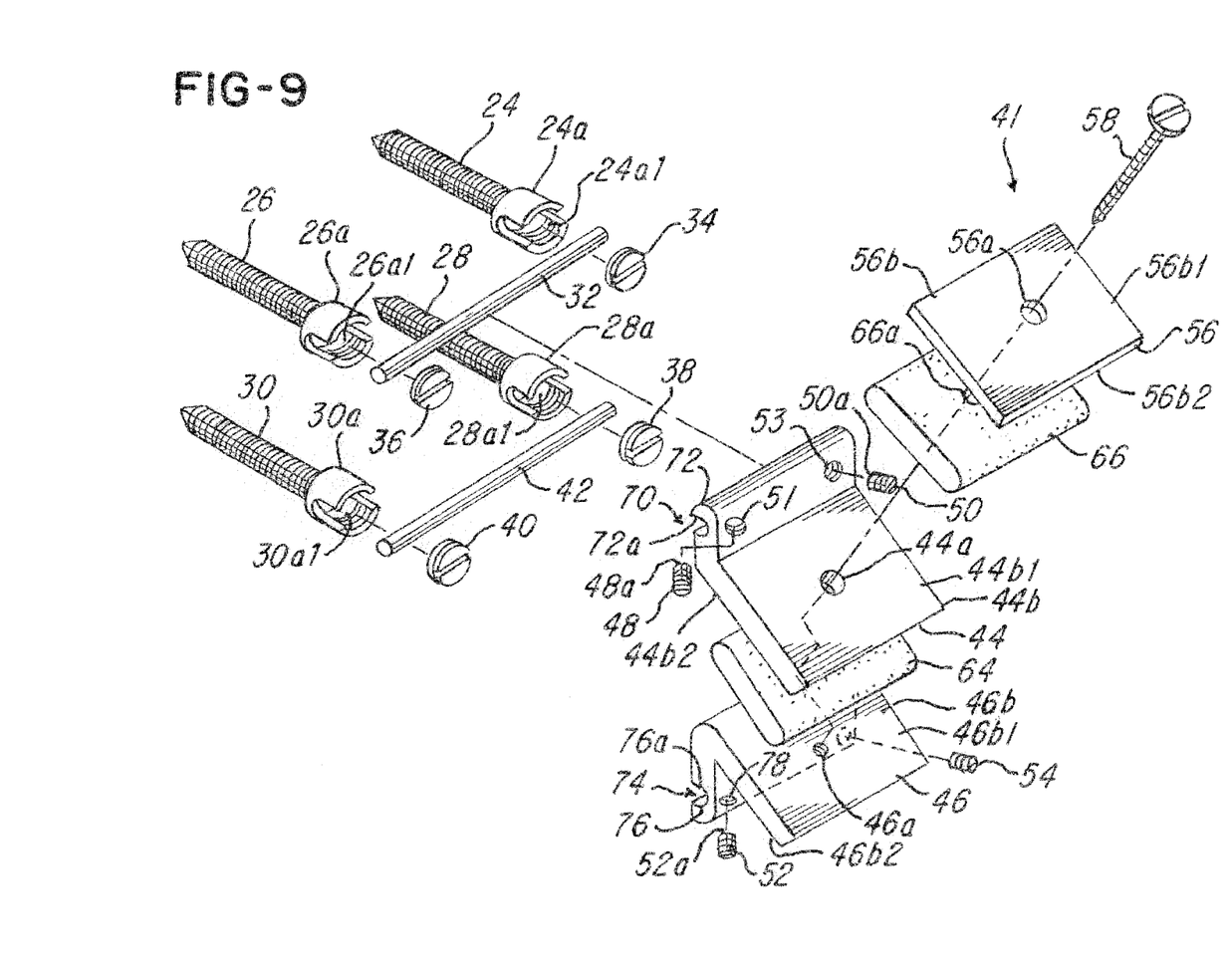
FIG. 9 is an exploded view of an embodiment of the inventions.

As illustrated in FIGS. 3, 4 and the exploded view in FIG. 9, the system 22 comprises a plurality of screws 24, 26, 28 and 30 comprising open heads 24a, 26a, 28a and 30a, respectively. In the embodiment being described, the open heads 24a, 26a, 28a and 30a comprise a receiving area 24a1, 26a1, 28a1 and 30a1, respectively. The areas 24a1, 26a1, 28a1 and 30a1 receive supports 32 and 42 as shown. For example, the open heads 24a and 26a receive a support or cylindrical rod 32 in the areas 24a1 and 26a1, respectively. The inner diameter of the heads 24a, 26a, 28a and 30a are threaded to threadably receive the screws 34, 36, 38 and 40 as described later herein.

Referring now to FIGS. 3, 4, 10 and 11, the screws 24, 26, 28 and 30 are first screwed into the vertebrae 16 and 20. The support 32 is situated in the areas 24a1 and 26a1. The heads 24a and 26a receive the screws 34 and 36 to secure the support 32 to the heads 24a and 26a as shown. Likewise, after the screws 28 and 30 are mounted to their respective vertebra, such as vertebra 20 in FIGS. 3 and 4, the support 42 is situated in the areas 28a1 and 30a1. The screws 38 and 40 are threadably received in the threaded screw heads 28a and 30a to lock the support 42 to the heads 28a and 30a.

Figure 10:
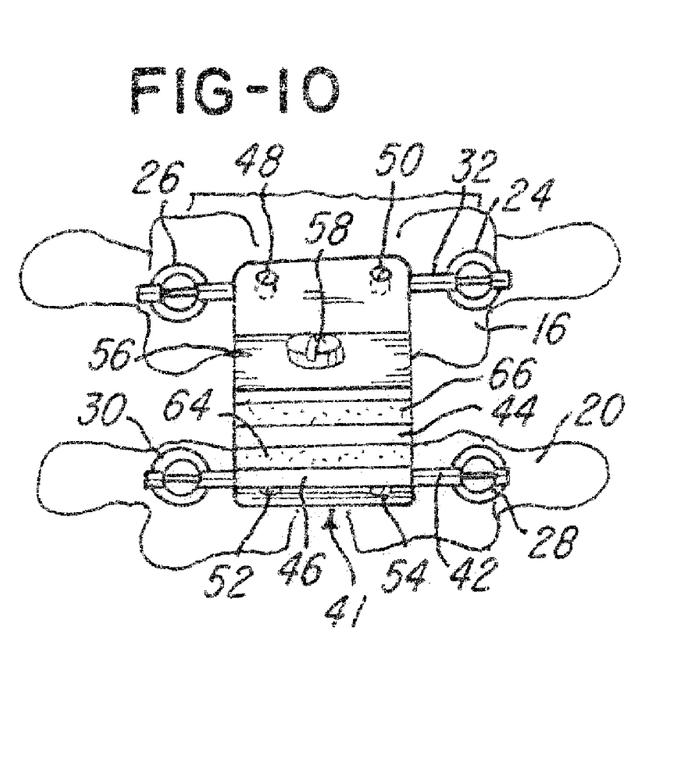
FIG. 10 is a rear view of a rear or posterior view of the retainer mounted on the supports.

The system 22 further comprises at least one retainer, retainer means or retaining system 41 (FIG. 5) for mounting on the supports 32 and 42 to supportably retain at least one compression body, such as a compression disk 64, exterior of an axis of the patient's spine. The retainer 41 comprises a first support 44 and a second support 46 which are mounted onto the rods 32 and 42, respectively, with appropriate fasteners or screws 48, 50, 52 and 54, as best illustrated in FIG. 10. A third support 56 may optionally be provided as well. Notice that the system 22 comprises an adjustable fastener or fastening means in the form of an adjustable fastener, tensioner or screw 58 that is received through the apertures 56a and 44a of supports 56 and 44 and threadably received in a threaded opening 46a of support 46.

Note that the support 44 comprises an aperture or recessed area 70 (FIG. 5) defined by a generally arcuate or curved wall 72. The support 32 is received in the area 70 and the screws 48 and 50 (FIG. 9) are threadably mounted in the threaded openings 51 and 53, respectively. The ends 48a and 50a of screws 48 and 50 engage the support 32 and force it against the surface 72a (FIG. 5) in order to mount and retain the support 44 on the rod 32. Likewise, the support 46 comprises an aperture 74 defined by an arcuate or curved wall 76 and having a surface 76a against which the support or rod 42 engages when the second support 46 is mounted thereto. In this regard and as illustrated in FIGS. 4, 9 and 10, note that the screws 52 and 54 are threadably received in threaded openings (e.g. threaded screw 52 is received in opening 78 in FIG. 9) until end 52a of screw 52 engages the support 42 and forces it against the surface 76a, thereby mounting and retaining the second support 46 onto the support 42

Figure 1:
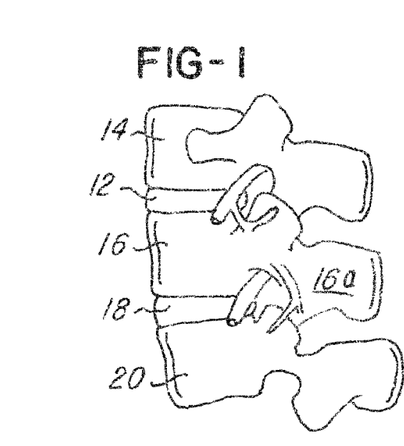
FIG. 1 is a view of a showing a disk situated between adjacent vertebrae.
Figure 2:
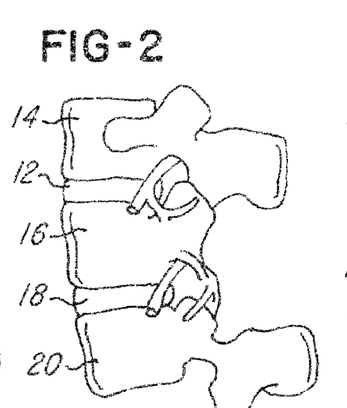
FIG. 2 is another view with part of the central vertebrae removed.
Figures 5, 6, 7:
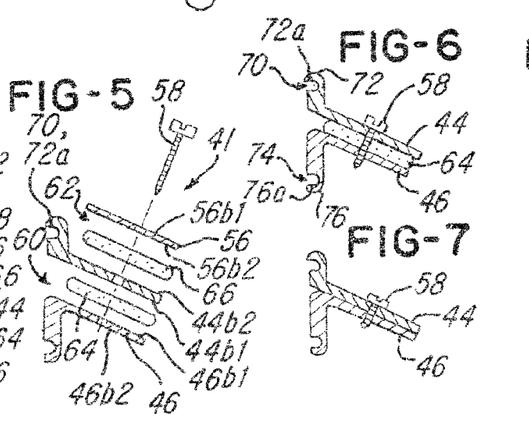
FIG. 5 is an exploded view of the retainer shown in a mounted position in FIG. 4.
FIG. 6 is a sectional view illustrating a single disk being used with a pair of support members.
FIG. 7 illustrates another feature of the invention used without a disk.

As illustrated in FIG. 5, note that the supports 44 and 46 cooperate to define a first compression body area 60, and supports 44 and 56 cooperate to define a second compression body area 62. The first and second compression body areas 60 and 62 receive at least one compression body, such as compression bodies or disks 64 and 66, respectively. In the embodiment being described, the compression body is a compressible material such as polyethylene, silicone, or viscoelastic polymer that comprises a mechanical density on the order of the native intervertebral disk. The compression bodies 64 and 66 may comprise any suitable cross-sectional and overall shape, such as one or more of the polygonal shapes illustrated in FIG. 8 or any oval, elliptical, circular or any other suitable or desired shape to provide the desired compression characteristics necessary to facilitate relieving or reducing load on at least one of the disks 12 or 18 (FIG. 1).

It should be understood, that the invention may be used with less than all three of the supports 44, 46, and 56 or with more supports as desired in a stacked or sandwiched array of supports and compression bodies, one on top of the other. As illustrated in FIG. 6, the system 22 could comprise just a pair of supports 44 and 46 between which one or more disks are mounted as shown in FIG. 6. Alternatively and as illustrated in FIG. 7, the supports could be provided without any compression disk therebetween to provide a fixed or fusion-type support to the vertebrae, such as vertebrae 16 and 20 illustrated in FIG. 4.

As illustrated in FIG. 5, the first and second supports 44 and 46 comprise portions 44b and 46b that lie in imaginary planes P1 and P2 (FIG. 4) that are generally parallel and are situated at an angle θ relative to the spinal axis when the system 22 is assembled and mounted into position illustrated in FIG. 4. Thus, the compression bodies 64 and 66 lie in one or more planes, such as planes P1 and P2, as illustrated in FIG. 4. In the embodiments being described, the angle θ is a predetermined angle of approximately 30 degrees or less. The angle generally corresponds to the angle between the long axis of the spine and the facet joints and/or spinous processes. Note that after the supports 44, 46 and 56 are mounted as shown, the compression bodies 64 and 66 are situated exterior to the spinal axis and spinal column, as illustrated in FIG. 4. In the embodiment being described, the planes P1 and P2 mentioned earlier are generally parallel to the facet joint and inter-spinous process articulations.

In the embodiment being described, the at least one adjustable fastener 58 is adjustable to permit loading at least one of the compression bodies 64 and 66 with a predetermined amount of pressure. In the embodiment being described, the predetermined amount of pressure is about 10-300 pounds. The predetermined amount of pressure may vary depending on the desired compliance and constraining properties of the device.

Note the supports 44, 46 and 56 each comprise a compression body support surface which in the embodiment being described is a planar portion 44b, 46b and 56b. Each of the generally planar portions 44b, 46b and 56b are arranged to define opposing surfaces 44b1 and 44b2, 46b1 and 46b2, and 56b1 and 56b2, respectively. Each surface cooperates with an opposing surface from an adjacent support to define the compression body receiving areas, such as the areas 60 and 62 (FIG. 5), mentioned earlier herein. For example, note that the support 44 in FIG. 5 comprises the surfaces 44b1 and 44b2. The surface 44b2 of support 44 cooperates with surface 56b1 of planar portion 56b to define the compression body receiving area 62. Likewise, the surface 44b1 of support 44 cooperates with surface 46b1 to define the compression body receiving area 60. The surfaces 44b1, 44b2, 46b1, 46b2, 56b1 and 56b2 may define a substantially continuous or flat surface for supporting all or a portion of the compression bodies 64 and 66, which as mentioned earlier, may be provided in any suitable shape. Alternatively, these surfaces may be non-planar. For example, the surfaces may be concave or define a recessed area (not shown) that generally corresponds to the shape of the compression body to facilitate retaining the compression body in place. In this regard, note that the compression bodies have an aperture, such as aperture 66a in body 66, that receives the adjustable fastener 58 to facilitate retaining the body in place.

Advantageously, the system and method of the present invention provide means for situating one or more artificial compression bodies exterior to the spinal column and exterior to the disk areas in which the patient's disks, such as disks 12 and 18, are situated.

Figure 8:
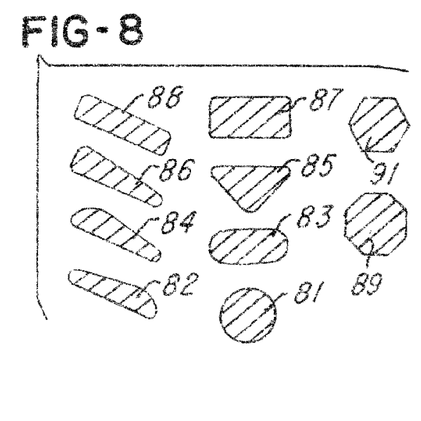
FIG. 8 illustrates a supply of compression bodies or disks of varying densities and sizes.

The compression bodies 64 and 66 (FIG. 5 and 9) are selected from a supply of a plurality of compression bodies comprising a plurality of different predetermined densities and/or a plurality of different predetermined shapes when viewed in cross section and/or a plan view. In the embodiment being described and as illustrated in FIGS. 8 and 9, the compression bodies 64, 66 and 81-91 in FIG. 8 may comprise a cross-sectional and overall shape that is polygonal, triangular, elliptical, circular, rectangular, square, or any other suitable shape desired.

As illustrated in the exploded view in FIG. 9, the compression bodies, such as compression bodies 64 and 66 shown in FIG. 9, may be generally rectangular to match or generally correspond to or complement the shape and size of the planar surfaces 44b1, 44b2, 46b1 and 56b2. Alternatively, different shapes and sizes, such as circular, triangular, polygonal, elliptical shaped disks may be provided. It should also be appreciated that the supports 44, 46 and 56 may be provided to define surface areas that are different from the shape of the portions 44b, 46b and 56b illustrated in FIG. 9. For example, the portions 44b, 46b and 56b could be triangular, polygonal, rectangular, elliptical or circular to define the portions 44b, 46b and 56b. In the embodiment being described, typical dimensions for the compressive body are 1-2 square inches by 0.5 to one inch. In the embodiment being described, the compression bodies 64, 66 and 81-91 may comprise predetermined densities on the order of the native intervertebral disks, which are selected based on the patient's needs.

During a surgical procedure, a portion 16a (FIG. 1) of vertebra 16 is removed by conventional means. Screws 24, 26, 28 and 30 are mounted into the vertebrae, such as vertebrae 16 and 20 in the illustration shown in FIG. 4. The supports 32 and 42 are then mounted on the screws 24-30 as shown and as described earlier. The retainer 41 comprising the first and second supports 44 and 46 are then mounted on the support rods 32 and 42, respectively. The disks 64 and 66 are sandwiched between the supports 44, 46 and 56 as shown and the adjustable tensioner 58 is mounted through the disks 64, 66 and supports 44 and 56 and threaded into threaded aperture 46a as illustrated in FIGS. 4 and 9.

As illustrated in FIGS. 4 and 10, if the vertebrae 16 and 20 move away from each other (as viewed in FIG. 4), then the support 44 moves in the direction of arrow A in FIG. 4 while supports 46 and 56 move in the direction of arrow B in FIG. 4. The movement of support 46 causes the support 56 to also move downward (as viewed in the Figure) in the direction of arrow B as the support 44 moves in the direction of arrow A. This, in turn, causes compressing of the compression disk 66, which facilitates reducing stress.

When the vertebrae 16 and 20 move toward each other, the support 44 moves downward in the direction of arrow B, while the supports 46 and 56 move in the direction of arrow A. The disk 64 compresses in response thereto, thereby facilitating reducing the compressive load on the patient's disk 18. The system and method are operable when a vertebra moves independently or when they move simultaneously with another vertebra to facilitate reducing loading on one or more disks, such as disk 18.

As alluded to earlier, the adjustable fastener 58 is adjustable so that a surgeon may preload or load one or more of the compression bodies 62 and 64 with a predetermined amount of pressure by simply rotating the fastener 58 in a clockwise direction. This may be desirable in order to decrease the freedom of movement of the device and decrease the compliance of the compression body based on the patient's needs.

Notice that the retainer 41 is situated posterior of and exterior to the spinal axis and the native disk spaces in which the disks, such as disks 12 and 18 in FIG. 1, are located. Thus, the system and method provide means and apparatus for situating one or more elastic or articulating mechanisms or bodies designed to replicate or augment the function of the native disk in any location other than the native disk space in which the patient's native disk is located. The system and method further permits the retainer 41 to be situated outside the axis of the spine.

Another advantage of the apparatus and system of the invention is that after the supports 44 and 46 are installed during a first operation, for example, a surgeon may replace the compressible disks, such as disk 64 and 66, with one or more new or replacement disks 64 and 66, such as a replacement disk (not shown) having a greater thickness, different density, different shape, different size or the like. Thus, the system and method of the present invention is adaptable and enables, for example, a surgeon to replace one or more of the compression bodies 64 and 66 with a replacement body (not shown) during subsequent operations. This can be done by using the same or a different retainer 41 in order to meet the needs of the patient.

Figure 11:
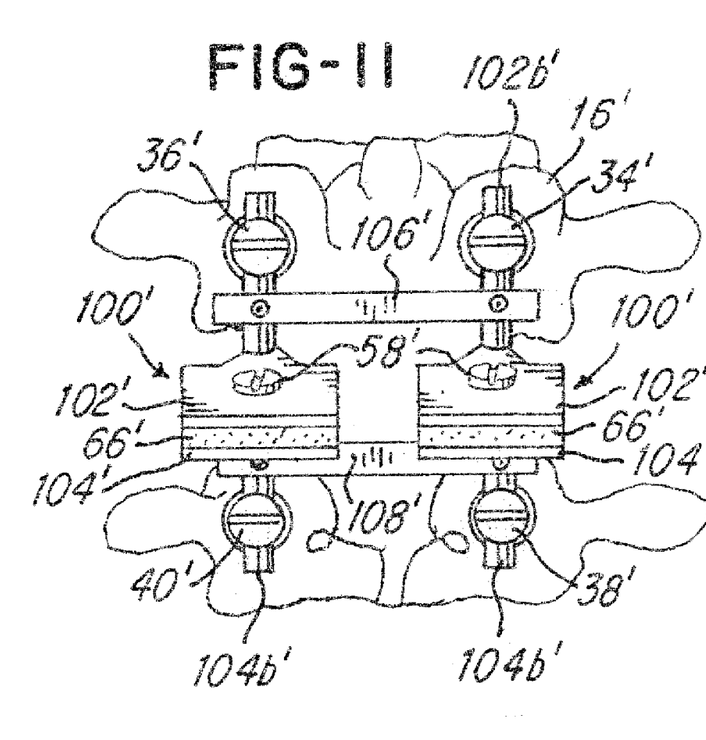
FIG. 11 is a view of another embodiment of the invention showing a plurality of retainers mounted on supports.
Figure 12:
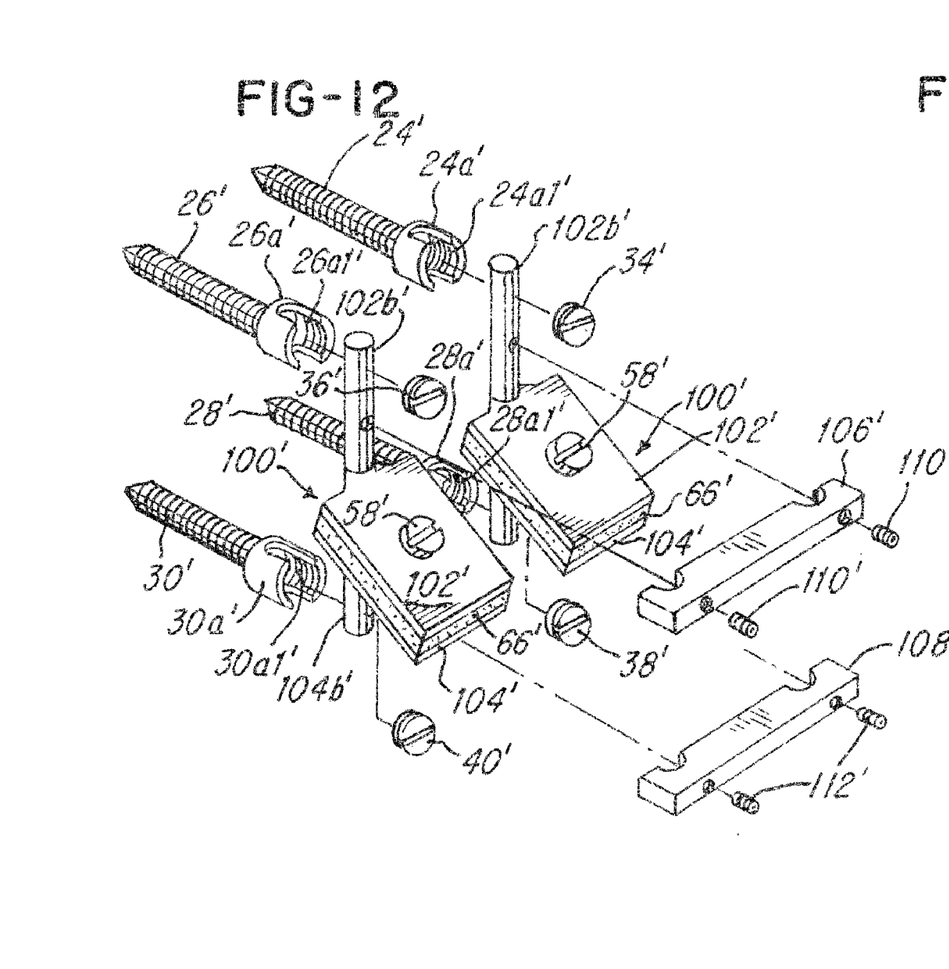
FIG. 12 is another view of another embodiment.
Figure 13:
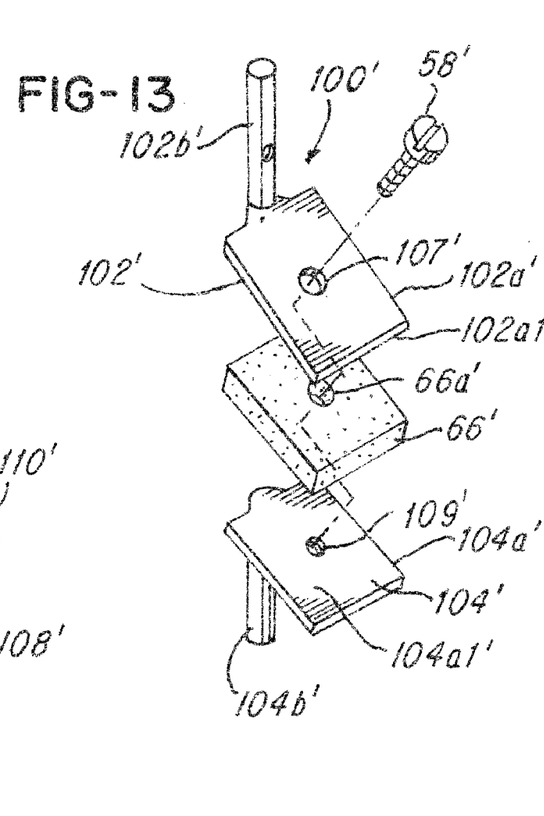
FIG. 13 is a view of a pair of supports used in another embodiment of the invention.

Referring now to FIGS. 11-13, another embodiment of the invention is shown wherein the system and method comprises a plurality of disk augmentation supports for facilitating reducing a load on at least one of the lumbar disks, when the vertebrae, such as vertebrae 14 and 16 (FIG. 1) move either away from or toward each other. This embodiment comprises parts that are the same or similar to the parts shown in FIGS. 1-10 and such parts are labeled with the same part number, except that the parts in FIGS. 11-13 have a prime mark ("'") added thereto. Notice in the embodiment shown in FIGS. 11-13 that a plurality of retainers 100' are provided. Each retainer 100' comprises a first support 102a' that is coupled to a support column or post 102b'. An opposing support 104' comprises a planar member 104a' that is coupled to a support post or column 104b'. Notice that the surfaces 102a1' and 104a1' are generally planar in the embodiment being described and support the compression disks 66' as shown. Similar to the embodiment shown in FIGS. 1-10, the supports 102b' and 104b' are secured to the screws 24'-30' with the screws 34'-40' in the same manner as the embodiment shown in FIGS. 1-10. The embodiment in FIGS. 11-13 further comprises a pair of retaining or spacing brackets 106' and 108' that are secured to the supports 102b' and 104b' with the screws 110' and 112', respectively. The brackets 106' and 108' facilitate retaining the retainers 100' in a fixed and spaced position relative to each other.

After the screws 24'-30' are mounted to the vertebrae, such as vertebras 16 and 20, respectively, the supports 102' and 104' of retainer 100' are secured thereto with the screws 34'-40'. The compression bodies 66' are then placed between surfaces 102a1' and 104a1' as shown and screw 58' is threaded through opening 107' (FIG. 13) and then threaded into the threaded aperture 109' to retain the compression body 66 between the supports 102' and 104'.

Advantageously, this embodiment of the invention utilizes the same or similar features as the embodiment illustrated in FIGS. 1-10 to facilitate reducing load on one or more disks in the spine or spinal column.

It should be understood that one or more of the features of the embodiment shown in FIGS. 1-10 may be used with the second embodiment. For example, the retainers 100' may be equipped with multiple disks like in FIG. 4, and those disks may be configured as shown in FIG. 8.

In this embodiment, a plurality of retainers 41 are provided to provide multiple support to adjacent vertebrae.

It should be understood that the invention may also be used in an environment where one or more disks are fused together, such as when a patient has transitional segment syndrome.

While the system and method described herein constitute preferred embodiments of this invention, it is to be understood that the invention is not limited to this precise system and method, and that changes may be made in either without departing from the scope of the invention, which is defined in the appended claims.

What is claimed is:

1. A disk augmentation system comprising:
a first support for mounting onto a first vertebra in a spinal column;
a second support for mounting onto a second vertebra;
said first and second supports being located exterior to a disk area between said first and second vertebrae and cooperating to define a first compression body area for receiving a first compression body; and
said first and second supports supporting said compression body exterior to said disk area, wherein said disk augmentation system further comprises:
a fourth support for mounting onto said first vertebra; and
a fifth support for mounting onto said second vertebra;
said fourth and fifth supports cooperating to define a second compression body area for receiving a second compression body;
said first and second supports supporting said first compression body in said first compression body area and being adapted to permit said first and second supports to become non-parallel during compression of said first compression body, said fourth and fifth supports supporting said second compression body in said second compression body area and being adapted to permit said fourth and fifth supports to become non-parallel during compression of said second compression body.

2. The disk augmentation system as recited in claim 1, wherein said disk augmentation system further comprises:
a bracket for coupling said fourth and fifth supports in a spaced relationship.

3. The disk augmentation system as recited in claim 1, wherein said fourth and fifth supports are situated adjacent to each other in a plane that generally corresponds to a patient's intervertebral disk.

4. An adjustable compression system for reducing a load on at least one lumbar disk, said adjustable compression system comprising:
a first retainer for mounting on a first vertebra and a second vertebra of a spinal column, said first retainer comprising a retaining area for receiving an artificial body and for supporting said artificial body exterior to an intervertebral disk space between said first and second vertebrae;
said first retainer cooperating with an artificial disk to facilitate reducing load on said at least one lumbar disk when said first and second vertebrae move either toward or away from each other, wherein said adjustable compression system comprises:
a second retainer for mounting on said first vertebra and second vertebra, said second retainer comprising a second retaining area for receiving a second artificial disk and supporting said second artificial disk posterior of said first and second vertebrae;

said first and second retainers each comprising at least one pair of supports that are adapted to become non-parallel to replicate or augment a function of a natural intervertebral disk.

5. The adjustable compression system as recited in claim 4 wherein said first retainer and said second retainer comprise at least one bracket for coupling to said first and second retainer in order to retain said first and second retainer in a fixed position relative to each other.

6. The adjustable compression system as recited in claim 4 wherein said first retainer and said second retainer comprise a pair of brackets for coupling to said first and second retainer in order to retain said first and second retainer in a fixed position relative to each other.

7. An adjustable compression system for reducing the load on at least one lumbar disk, said adjustable compression system comprising:
  a first retainer for retaining a first compression body exterior to a spinal column and for facilitating reducing load on at least lumbar disk in said spinal column; and
  a second retainer for mounting on said spinal column also for facilitating reducing load on said at least one lumbar disk;
  wherein said first and second retainers are not located along an axis of said spinal column;
  said first and second retainers each comprising at least one pair of supports that are adapted to become non-parallel to replicate or augment a function of a natural intervertebral disk.

8. The adjustable compression system as recited in claim 7 wherein the adjustable compression system further comprises;
  at least one bracket coupled to said first and second retainers for securing said first and second retainers in a fixed position relative to each other.

9. The adjustable compression system as recited in claim 7 wherein the adjustable compression system further comprises;
  a plurality of brackets coupled to said first and second retainers for securing said first and second retainers in a fixed position relative to each other.

10. The adjustable compression system as recited in claim 7 wherein said first compression body is selected from a supply of a plurality of artificial bodies, said plurality of artificial bodies comprising different predetermined densities.

11. The adjustable compression system as recited in claim 7 wherein said first compression body is selected from a supply of a plurality of artificial bodies, said plurality of artificial bodies comprising different predetermined shapes.

12. The adjustable compression system as recited in claim 8 wherein at least one of said first or said second retainer comprises:
  a first mount for mounting on a first vertebra and a second mount for mounting on a second vertebra, said first mount comprising a first artificial body support and said second mount comprising a second artificial body support;
  said first and second artificial body supports cooperating to define a receiving area.

13. The adjustable compression system as recited in claim 12 wherein said first and second mounts detachably receive said first and second artificial body supports after said first and second mounts are mounted on said first and second vertebrae.

14. The adjustable compression system as recited in claim 13 wherein said adjustable compression system comprises at least one fastener for adjustably fastening said first and second artificial body supports to said first and second mounts.

15. The adjustable compression system as recited in claim 13 wherein said adjustable compression system comprises at least one adjustable fastener to permit adjustable loading said first compression body with a predetermined amount of pressure after it is received in the receiving area.

16. The adjustable compression system as recited in claim 15 wherein said predetermined amount of pressure is on the order of the physiological pressures upon the native intervertebral disk.

17. The adjustable compression system as recited in claim 12 wherein said first and second artificial body supports are generally planar.

18. The adjustable compression system as recited in claim 12 wherein said first and second mounts each comprise at least one mounting rod;
  said first and second artificial body supports being mounted on said at least one mounting rod such that said first and second artificial body supports are situated in a generally opposed relationship exterior to said spinal column.

19. The adjustable compression system as recited in claim 12 wherein said first artificial body support comprises a first planar member and said second artificial body support comprises a second planar member, said first and second planar members being in a generally parallel relationship after said first and second mounts are mounted on said first and second vertebrae, respectively.

20. The adjustable compression system as recited in claim 19 wherein said first and second planar members are situated at a predetermined angle relative to said spinal column.

21. The adjustable compression system as recited in claim 20 wherein said predetermined angle is acute.

22. The adjustable compression system as recited in claim 20 wherein said predetermined angle faces downward at approximately 30 degrees.

23. The adjustable compression system as recited in claim 12 wherein said adjustable compression system comprises a third mount that cooperates with at least one of said first and second mounts for reducing spinal column loads when said first and second vertebrae move in opposite directions.

24. The adjustable compression system as recited in claim 23 wherein said third mount and at least one of said first or second mounts defines a second compression body receiving area for receiving a second artificial body.

25. The adjustable compression system as recited in claim 24 wherein said first mount comprises a first planar member, said second mount comprises a second planar member, and said third mount comprises a third planar member, said first, second and third mounts being in a generally parallel relationship after said first, second and third mounts are mounted on a frame.

26. The adjustable compression system as recited in claim 25 wherein said first, second and third planar members are situated at a predetermined angle relative to said spinal column.

27. The adjustable compression system as recited in claim 26 wherein said predetermined angle is an acute angle.

28. The adjustable compression system as recited in claim 27 wherein said predetermined angle faces downward at approximately 30 degrees.

29. The adjustable compression system as recited in claim 25 wherein said adjustable compression system comprises at least one fastener for adjustably fastening said first, second and third mounts together to permit loading said first and second compression bodies with a predetermined amount of pressure.

30. The adjustable compression system as recited in claim 29 wherein an adjustable tensioner comprises a screw for adjustably securing said first, second and third mounts together.

31. The adjustable compression system as recited in claim 24 wherein said first compression body and said second compression body are selected from a supply of a plurality of artificial bodies, said plurality of artificial bodies comprising different predetermined densities.

32. The adjustable compression system as recited in claim 31 wherein said first compression body and said second compression body comprise a compressible material.

33. The adjustable compression system as recited in claim 32 wherein said compressible material is at least one of polyethylene, silicone, or viscoelastic polymer.

34. The adjustable compression system as recited in claim 24 wherein said first compression body and said second compression body are selected from a supply of a plurality of artificial bodies, said plurality of artificial bodies comprising different predetermined shapes.

35. The adjustable compression system as recited in claim 34 wherein said predetermined shapes comprises circular, triangular, elliptical or polygonal.

36. The adjustable compression system as recited in claim 24 wherein at least one of said first vertebra or said second vertebra is fused to a third vertebra.

* * * * *